United States Patent [19]
Gross et al.

[11] Patent Number: 5,216,025
[45] Date of Patent: Jun. 1, 1993

[54] NITRIC OXIDE SYNTHESIS INHIBITORS FOR POTENTIATING THE ACTION OF PRESSOR AGENTS IN CERTAIN HYPOTENSIVE PATIENTS

[75] Inventors: Steven S. Gross, New York, N.Y.; Robert G. Kilbourn, Houston, Tex.; Roberto Levi, New York, N.Y.

[73] Assignees: Board of Regents, The University of Texas System, Austin, Tex.; Cornell Research Foundation, Inc., Ithaca, N.Y.

[21] Appl. No.: 723,480

[22] Filed: Jul. 1, 1991

Related U.S. Application Data

[63] Continuation-in-part of PCT/US90/05199 filed Sep. 13, 1990, which is a continuation-in-part of Ser. No. 406,909, Sep. 13, 1989, Pat. No. 5,028,627.

[51] Int. Cl.$^5$ .................. A61K 31/195; A61K 37/00
[52] U.S. Cl. .................. 514/565; 514/12; 514/930; 424/85.1; 424/85.2; 424/85.5
[58] Field of Search .................. 514/565, 12, 930; 424/85.1, 85.2, 85.5

[56] References Cited

U.S. PATENT DOCUMENTS

| | | | |
|---|---|---|---|
| 4,282,217 | 8/1981 | Baglioni et al. | 424/240 |
| 4,734,438 | 3/1988 | Macri | 514/653 |
| 5,028,627 | 7/1991 | Kilbourn et al. | 514/565 |
| 5,059,712 | 10/1991 | Griffith | 562/560 |

FOREIGN PATENT DOCUMENTS

| | | |
|---|---|---|
| 92/05570 | 9/1992 | PCT Int'l Appl. |
| 90/05199 | 9/1990 | World Int. Prop. O. |

OTHER PUBLICATIONS

Stuehr, D. J. et al, Synthesis of Nitrogen Oxides from L-Arginine by Macrophage Cytosol: Requirement for Inducible and Constitutive Components, *Biochem, Biophys. Res. Commun.*, (1989) vol. 161, 420–426.

Stuehr, D. J. et al., Activated Murine Macrophages Secrete a Metabolite of Arginine with the Bioactivity of Endothelium-Derived Relaxing Factor and the Chemical Reactivity of Nitric Oxide, *J. Exp. Med.*, (1989) vol. 169, 1011–1020.

Rees, D. D. et al., Role of Endothelium-Derived Nitric Oxide in the Regulation of Blood Pressure, *Proc. Natl. Acad. Sci. U.S.A.*, (1989) vol. 86, 3375–3378.

Aisaka, K. et al., $N^G$-Methylarginine, An Inhibitor of Endothelium-Derived Nitric Oxide Synthesis, is a Potent Pressor Agent in the Guinea Pig: Does Nitric Oxide Regulate Blood Pressure in vivo, *Biochem. Biophys. Res. Commun.* (1989) 160:881–886.

(List continued on next page.)

Primary Examiner—Allen J. Robinson
Assistant Examiner—Gary E. Hollinden
Attorney, Agent, or Firm—Arnold, White & Durkee

[57] ABSTRACT

A method for treatment of an animal for systemic hypotension induced by internal nitric oxide production caused by endotoxin or cytokines. The method involves administering an $\alpha_1$ adrenergic agonist and an amount of an inhibitor of nitric oxide formation from arginine to restore vascular contractile sensitivity to $\alpha_1$ adrenergic agonists. A preferred inhibitor of nitric oxide formation is an $N^G$-substituted arginine having at least one hydrogen on a guanidino amino group replaced by another atomic or molecular species, including $N^G$-aminoarginine, $N^G$-nitroarginine, and $N^G$-alkylarginines such as $N^G$-methylarginine, $N^G$-ethylarginine, $N^G$-propylarginine and $N^G$-butylarginine. Arginine derivative inhibitors are preferably of the L configuration and include pharmaceutically acceptable addition salts. Treatment of systemic hypotension in a patient which has been induced by chemotherapy with biologic response modifiers such as tumor necrosis factor or interleukin-2 may be likewise accomplished. Treatment of an animal for systemic hypotension induced by endotoxin, or other bacterial toxins, e.g., septic shock, may also be accomplished by treatment with $\alpha_1$ adrenergic agonists and an inhibitor such as an arginine derivative, restoring vascular contractile sensitivity to the $\alpha_1$ adrenergic agonists.

27 Claims, 4 Drawing Sheets

OTHER PUBLICATIONS

Natanson, C. et al., Endotoxin and Tumor Necrosis Factor Challenges in Dogs Simulate the Cardiovascular Profile of Human Septic Shock, *Journal of Exp. Med.* (1989) 169:823–832.

Schmidt, H. et al., Arginine is a Physiological Precursor of Endothelium-Derived Nitric Oxide, *Eur. J. of Pharmacology* (1988) 154:213–216.

Palmer, R. M. J. et al., L-Arginine is the Physiological Prescursor for the Formation of Nitric Oxide in Endothelium-Dependent Relaxation, *Biochem. Biophys. Res. Commun.* (1988) 153:1251–1256.

Sakuma, I. et al., Identification of Arginine as a Precursor of Endothelium-Derived Relaxing Factor, *Proc. Natl. Acad. Sci U.S.A.* (1988) 85:8664–8667.

Palmer, R. M. J. et al., Vascular Endothelial Cells Synthesize Nitric Oxide from Arginine, *Nature,* (1988) vol. 333, 664–666.

Hibbs, J. B. et al., Nitric Oxide: A Cytotoxic Activated Macrophage Effector Molecule, *Biochem. Biophys. Res. Commun.* (1988) 157:87–94.

Marletta, M. A. et al., Macrophage Oxidation of L-Arginine to Nitrite and Nitrate: Nitric Oxide is an Intermediate, *Biochemistry* (1988) 27:8706–8711.

Palmer, R. M. J. et al., Nitric Oxide Release Accounts for the Biological Activity of Endothelium-Derived Relaxing Factor, *Nature* (1987) 327:524–526.

Stuehr, D. J. et al., Induction of Nitrite/Nitrate Synthesis in Murine Macrophages by BCG Infection, Lymphokines, or Interferon-Δ, *J. of Immunology* (1987) 139:518–525.

Iyengar, R. et al., Macrophage Synthesis of Nitrite, Nitrate and N-Nitrosamines: Precursors and Role of the Respiratory Burst, *Proc. Natl. Acad. Sci. U.S.A.* (1987) vol. 84, 6369–6373.

Turan et al., *Acta Chimica Academiae Scientiarum Hungaricae* (1975) 85:327–332.

Kilbourn et al., $N^G$-Methyl-L-Arginine Inhibits Tumor Necrosis Factor-Induced Hypotension: Implications for the Involvement of Nitric Oxide, *Proc. Natl. Acad. Sci. U.S.A.* (1990) 87:6329–3632.

NITRIC OXIDE SYNTHESIS INHIBITORS FOR POTENTIATING THE ACTION OF PRESSOR AGENTS IN CERTAIN HYPOTENSIVE PATIENTS

Research relating to the development of this invention was supported by the United States Public Health Service grants which gives the United States government certain rights to use of the present invention.

This is a continuation-in-part of international application PCT/US90/05199 filed Sep. 13, 1990, which is a continuation-in-part of U.S. Ser. No. 07/406,909 filed Sep. 13, 1989, to issued as U.S. Pat. No. 5,028,627 on Jul. 2, 1991, both of which have an inventor and assignee in common and are incorporated by reference herein for all pertinent supporting data demonstrating the effects of arginine derivatives on NO production and concomitant vascular effects.

BACKGROUND OF THE INVENTION

The present invention relates to the alleviation of hypotension induced by activators of nitric oxide production, particularly as related to the restoration of sensitivity to known pressor agents such as $\alpha_1$ adrenergic agonists.

It is a well known clinical observation that septic or cytokine-induced shock patients are insensitive to clinically used pressor agents. The basis for this insensitivity was not understood until now. The present invention is a means to restore pressor sensitivity in this clinical class of patients, based on the discovery that nitric oxide overproduction is the basis for pressor insensitivity.

In 1980, Furchgott and Zawadski (Nature 288: 373-376) demonstrated that endothelial cells, which line blood vessels, can be stimulated to release a substance which relaxes vascular smooth muscle i.e., causes vasodilatation. Since the chemical nature of this substance was completely unknown, it was simply named endothelium-derived relaxing factor (EDRF). It is now widely accepted that many naturally-occurring substances which act as physiological vasodilators mediate all or part of their action by stimulating release of EDRF; these substances include, acetylcholine, histamine, bradykinin, leukotrienes, ADP, ATF, substance P, serotonin, thrombin and others. Although the extremely short lifetime of EDRF (several seconds) hampered efforts to chemically identify this molecule, in 1987 several laboratories suggested that EDRF may be nitric oxide (NO), which spontaneously decomposes to nitrate and nitrite. A fundamental problem in accepting this NO hypothesis was that mammalian systems were not known to contain an enzymatic pathway which could synthesize NO; additionally, a likely precursor for NO biosynthesis was unknown. After observing that the arginine analog L-N$^G$-methylarginine (L-NMA) could inhibit vascular EDRF/NO synthesis induced by acetylcholine and histamine, and that EDRF/NO synthesis could be restored by adding excess L-arginine, it was proposed that arginine is the physiological precursor of EDRF/NO biosynthesis (Sakuma et al., PNAS 85: 8664-8667, 1988). Additional evidence supporting this proposal was reported almost simultaneously. It was later demonstrated that inhibition of EDRF/NO synthesis in the anesthetized guinea pig raises blood pressure, suggesting that EDRF/NO is an important physiological regulator of blood pressure (Aisaka et al., BBRC 160: 881-886, 1989). Notwithstanding the accumulated evidence supporting a role for NO in vascular homeostasis, it is understood by those skilled in the art that other nitrogen oxides may be present and may be active in reducing blood pressure. Within this specification, the acronym NO will be understood to represent nitric oxide and any additional vasoactive nitrogen oxides.

Other laboratories had demonstrated that macrophage cells become "activated" by 12-36 hour treatment with gamma-interferon, bacterial endotoxin and various cytokines. This "activation" is associated with initiation of tumor cell killing and generation of nitrite and nitrate from L-arginine. It was observed that activated macrophages actually make NO from L-arginine (just like endothelial cells) and that this NO subsequently reacts with oxygen to form more oxidized nitrogen metabolites which appear to be physiologically inert (Stuehr et al., J. Exp. Med. 169: 1011-1020, 1989). The enzyme responsible for NO synthesis (nitric oxide synthetase) has been partially characterized (Stuehr et al. BBRC161: 420-426, 1989) and acts to oxidize the terminal amino group of arginine, resulting in production of NO and citrulline. It is now believed that macrophage-derived NO is an important tumoricidal and bactericidal agent. Since bacterial endotoxin, gamma-interferon and other cytokines can trigger NO generation by macrophage cells (which are not known to play a role in vasoregulation) it appeared possible that: 1) NO generation may also be stimulated by similar stimuli in other cell types in the vessel wall that do impact on vascular tone and 2) septic shock (i.e., systemic vasodilatation induced by bacterial endotoxin) may result from massive activation of NO biosynthesis. Speculation that the latter hypothesis was correct was fueled by a prior report that urinary nitrate levels are grossly elevated by treatment of rats with bacterial endotoxin (Wagner et al., PNAS 80: 4518-4521, 1983).

Cytokines are well known to cause morphological and functional alterations in endothelial cells described as "endothelial cell activation". Distinct immune-mediators such as tumor necrosis factor (TNF), interleukin-1 (IL-1), and gamma-interferon (IFN or I) appear to induce different but partially overlapping patterns of endothelial cell activation including increased procoagulant activity (Bevilaqua, 1986), PGI2 production (Rossi, 1985 Science 229,174), HLA antigen expression (Pober 1987) and lymphocyte adhesion molecules (Harlan 1985; Cavender 1987). Although these cytokines are reported to cause hypotension, vascular hemorrhage, and ischemia, the underlying mechanisms of altered vasoactivity are unclear (Goldblum et al. 1989; Tracey et al. Science 234:470, 1986). A potential mediator of altered vasoactivity is EDRF.

In both clinical and animal (Dvorak, 1959) studies on the effects of biological response modifiers, a major dose limiting toxicity has been hypotension and vascular leakage.

The use of arginine-based inhibitors of nitric oxide synthesis for the treatment of endotoxin(sepsis)- and cytokine-induced hypotension relates to the discovery that nitric oxide, a potent vasodilator, is overproduced in these conditions.

While pressor drug therapy (i.e., adrenergic agonists) is a commonly employed method for attempting to restore blood pressure in septic patients, pressor agents are typically ineffective in these patients (a significant fraction subsequently dying). Indeed, insensitivity to vasoconstrictors is a characteristic of septic shock and considered to be a major impediment to effective pharmacotherapy. The mechanistic basis for this insensitivity of septic blood vessels of vasoconstrictors is incompletely understood.

On the other hand, it has been known for many years that nitric oxide dilates isolated blood vessels which had been previously constricted with various pressor agents. Thus NO is known to reverse the action of vasoconstrictors in vitro. More recently, the present inventors have found that endotoxin and cytokines induce the synthesis of large quantities of nitric oxide in the blood vessel wall. Taken together, these observations suggested the possibility that excess nitric oxide synthesis may be the cause of pressor drug efficacy in septic patients. The findings presented herein support this view and indicate that inhibition of arginine-derived nitric oxide synthesis will, in addition to restoring blood pressure, restore pressor sensitivity in septic patients.

SUMMARY OF THE INVENTION

The present invention involves a method for treatment of a patient having systemic hypotension induced by sepsis or a biological response modifier such as the cytokine IFN, TNF, IL-1 and/or IL-2. Hypotension of this sort is characteristically unresponsive to pressor agents. The present invention relates to the presently described discovery that this unresponsiveness is due to NO overproduction. The method of the present invention involves administering, preferably intravascularly, an amount of an inhibitor of nitric oxide formation from arginine to restore sensitivity to pressor agents such as $\alpha_1$ adrenergic agonists. This is in conjunction with administration of an $\alpha_1$ adrenergic agonist or other pressor. Although preferable administration of one or both of the $\alpha_1$ adrenergic agonist and NO production inhibitor is intravascular, it is contemplated that other parenteral administration routes such as intraperitoneal, intramuscular or subdermal injection, for example, may prove useful when appropriate. Enteral or topical administration of the NO synthesis inhibitor may also prove beneficial for certain clinical conditions concomitantly involving the use of known pressor agents for restoring blood pressure. It is contemplated that the nitric oxide synthesis inhibitor will be administered prior to the $\alpha_1$ adrenergic agonist, although efficacy is anticipated if the order were reversed. Known $\alpha_1$ adrenergic agents include phenylephrine, epinephrine, norepinephrine, dopamine, metaraminol, methoxamine, ephedrine, and mephentermine.

In one embodiment the inhibitor of NO synthesis from arqinine is an arqinine derivative such as $N^G$-substituted arqinine or an $N^G,N^G$-disubstituted arginine (i.e., one or more guanidino group hydrogen replacements) which is administered to a patient with an $\alpha_1$ adrenergic agonist experiencing NO-induced systemic hypotension. The arginine derivatives of the present invention are preferably of the L configuration and include any pharmaceutically acceptable addition salts as commensurate with planned treatments.

One particular use of the method of the present invention is for treatment of systemic hypotension induced in a patient by chemotherapeutic treatment with tumor necrosis factor, interleukin-2 or both. In this aspect, the method involves administering to the chemotherapy patient a known $\alpha_1$ adrenergic pressor agent and an amount of an inhibitor of NO production from arginine such as $N^G$-substituted arginine or $N^G,N^G$-disubstituted arginine. The amount is effective to restore vascular sensitivity to stimulation by $\alpha_1$ adrenergic agonists.

An important aspect of the present invention is as a method for treatment of a patient for systemic hypotension induced by a bacterial toxin such as endotoxin, i.e., septic shock. The treatment involves administering to such a hypotensive patient one or more selected known pressor agents such as $\alpha_1$ adrenergic agonists including phenylephrine, epinephrine, norepinephrine, dopamine, metaraminol, methoxamine, ephedrine, and mephentermine as well as an amount of an inhibitor of NO production from arginine. Such inhibitors include $N^G$-substituted arginine, $N^G,N^G$-disubstituted arginine, $N^G$-aminoarginine or $N^G$-nitroarginine effective to promote responsiveness to pressor agents such as $\alpha_1$ adrenergic agonists or angiotensin.

Septic shock is a life-threatening condition that results from exposure to bacterial toxins such as endotoxin. It is manifested by cardiovascular collapse and mediated by the release of cytokines such as tumor necrosis factor and interleukin-1. Some of these cytokines cause the release of vasoactive substances. Nitric oxide overproduction is an important contributor to endotoxic shock. Moreover, the present findings demonstrate for the first time, the utility of nitric oxide synthesis inhibitors combined with $\alpha_1$ adrenergic agonists in the treatment of endotoxic shock and suggest that such use may be of therapeutic value in the treatment of septic shock.

Preferred inhibitors of NO synthesis are $N^G$-substituted arginine derivatives of the L configuration for uses as described herein include $N^G$-aminoarginine, $N^G$-nitroarginine, and $N^G$alkyl arginines such as $N^G$-methylarginine, $N^G$-ethylarginine, $N^G$-propylarginine and $N^G$-butylarginine. Effective amounts of the substituted or disubstituted arginine derivatives inhibit production in a patient of nitric oxide from arginine, thus the hypotensive effects and loss of sensitivity to $\alpha_1$ adrenergic or other pressor agents due to excess NO are prevented. Those skilled in the art recognize that a variety of other guanidino substituents may likewise be used. These include hydroxyalkyl and other alkyl or alkenyl variants.

In a more general sense, the present invention may relate to a method for treatment of an animal for any systemic hypotension related to induced production of nitric oxide. Said method involves intravascularly administering to an animal a pressor an a NO production inhibitor such as an arginine derivative in an amount inhibiting production of nitric oxide from arginine to aid in restoration of sensitivity to pressors such as $\alpha_1$ adrenergic agents. Effective inhibitors of NO synthesis from arginine include a wide variety of compounds, particularly arginine derivatives and the like. Many substituents other than hydrogen on the guanidino group of arginine or arginine analogous guanidino functional groups should serve as well. Synthesis of hypotension-producing nitric oxide may be directly or indirectly induced by interferon (IFN), tumor necrosis factor (TNF), interleukin-1 (IL-1), interleukin-2 (IL-2) and endotoxin. In a preferred aspect, the arginine derivatives usable as described herein include $N^G$-substituted or $N^G,N^G$ disubstituted arginine. In one embodiment, these inhibitors preferably have guanidino linked alkyl substituents selected from the group consisting of methyl, ethyl, propyl and butyl. Analogous derivatives may include modified alkyl substituents such as hydroxyalkyl, carboxyalkyl and aminoalkyl. The arginine derivatives usable in the practice of the present invention most preferably comprise arginine with at least one $N^G$ guanidino substituent selected from the group consisting of lower alkyl, hydroxyalkyl, and alkenyl. The effective amount of NO synthesis inhibitors of the present invention is an amount sufficient to inhibit production of nitric oxide from arginine.

DESCRIPTION OF THE PREFERRED EMBODIMENTS

Figure 1A:
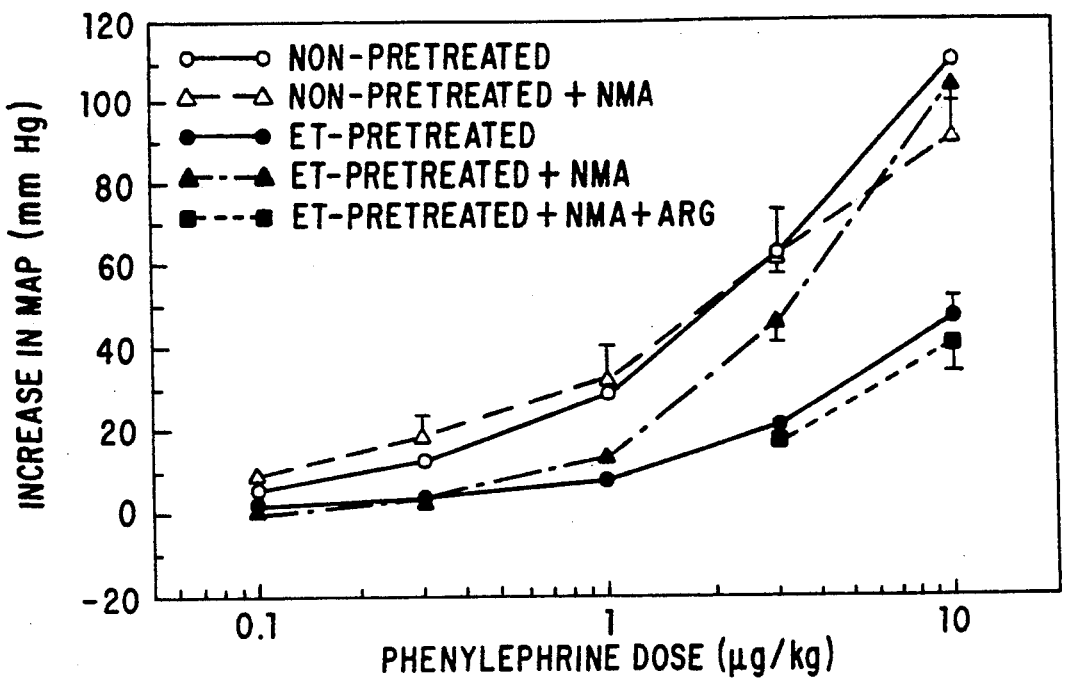
FIGS. 1A and 1B depict the effect of endotoxin pretreatment on peak pressor responses to phenylephrine (FIG. 1A) and angiotensin II (FIG. 1B) in pithed rat. Animals were either untreated (control) or treated with endotoxin (LPS-treated; 15 mg/kg, i.p.) 6 hours prior to their being pithed and instrumented for blood pressure recording.

The present invention involves a finding that endotoxin-induced insensitivity to pressor agents can be restored by inhibitors of nitric oxide synthesis.

Clinical studies of biologic response modifiers such as certain cytokines including tumor necrosis factor, interleukin-1, interleukin-2 and gamma-interferon, have shown that a major dose-limiting toxicity is hypotension.

Since hypotension is responsive to biological response modifiers and mediated by nitric oxide production, the utility of pressor agents for therapy of hypotension in these patients will be enhanced by nitric oxide synthesis inhibitors of which arginine analogs or derivatives are a major type.

The present inventors note herein that NO production in the vascular wall appears to play a role in the development of hypotension and contributes to the insensitivity to pressor agents associated with bacterial toxins and biological response modifiers such as certain cytokines.

Hypotension is frequently treated by the administration of $\alpha_1$ adrenergic pressor agents such as, for example, phenylephrine, epinephrine, norepinephrine, dopamine, metaraminol, methoxamine, ephedrine, and mephentermine. For hypotension associated with endotoxic shock or treatment with various cytokines, these drugs no longer retain their effectiveness. A central part of the present invention involves the discovery that if NO production from arginine is inhibited, loss of vascular sensitivity to pressor agents may be restored.

These results which follow demonstrate that arginine-derived or other nitric oxide synthesis inhibitors (e.g., $N^G$-substituted arginine or arginine analogs) will be useful for the clinical treatment of endotoxin (sepsis)- and cytokine-induced hypotension by a mechanism in addition to the direct increase in blood pressure described in U.S. Pat. No. 5,028,657. The above exemplary findings indicate that the efficacy of pressor drugs currently employed for the treatment of hypotension, but largely ineffective in conditions such as NO-induced hypotension, will have enhanced efficacy after administration of a nitric oxide synthesis inhibitor by intravenous bolus or infusion. Thus, this invention should increase the efficacy of currently employed pharmacotherapy with pressor drugs (e.g., alpha-adrenergic and dopaminergic agonists). An additional application of this invention is that the combined NO synthesis inhibitor/pressor therapy may reduce the dosage of an inhibitor such as an arginine analog required to achieve therapeutic benefit, thereby diminishing the frequency of possible toxic side-effects of nitric oxide synthesis inhibitors.

It is understood that those skilled in the art may obtain or design and prepare many other inhibitors of NO production that would function as well or even better than the specific ones described herein. These examples demonstrate:

(1) That in response to endotoxin, animals become insensitive to pressor agents similar to that observed in patients with septic shock. Inhibitors of nitric oxide synthesis restore pressor sensitivity in vivo.

(2) Ex vivo aortae isolated from endotoxin-treated rats show a progressive decline in pressor sensitivity.

(3) The time course of increase in plasma nitrate in endotoxin treated rats follows an identical time course of ex vivo development of pressor sensitivity.

(4) Restoration of pressor sensitivity in ex vivo endotoxic vessels occurs with each of several arginine antagonists.

The following examples are presented to describe best modes, preferred embodiments and utilities of the present invention and are not meant to limit the present invention unless otherwise specifically stated in the claims appended hereto.

EXAMPLE 1

In vivo Testing

Figure 1B:
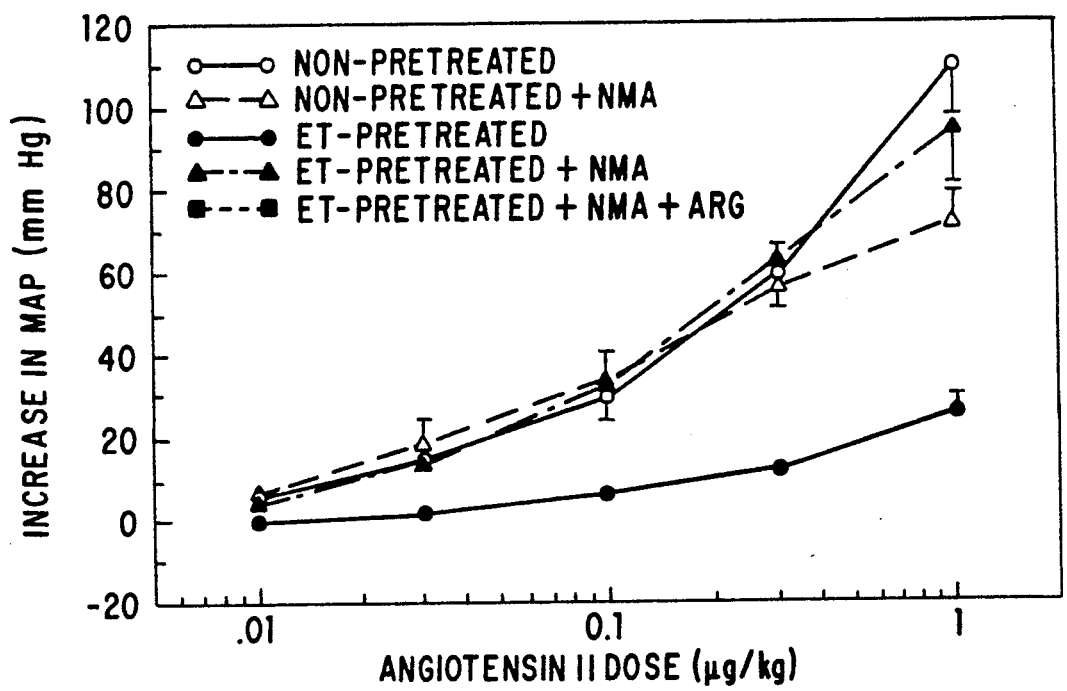

To establish that nitric oxide overproduction can result in a diminished sensitivity to pressor agents, studies in a rat model of septic hypotension, i.e., the endotoxic-, pithed-rat, were performed. FIGS. 1A and 1B show the effect of endotoxin (ET or LPS abbreviation) pretreatment on peak pressor responses to phenylephrine (FIG. 1A) and angiotensin II (FIG. 1B) in pithed rat. Animals were either untreated (control) or treated with endotoxin (LPS-treated; 15 mg/kg, i.p.) 6 hours prior to their being pithed and instrumented for blood pressure recording. Prior to pithing, mean systematic arterial pressure in control rats was $123\pm3$ mm Hg (n=6). Pressure fell to $59.8\pm3$ mm Hg after pithing of control animals nd was further significantly reduced to $28.7\pm2.1$ mm Hg after pithing LPS-treated animals ($P<0.01$ by Student's t-test, n=6). Initial blood pressure in NMA ($N^G$ methyl-L-arginine)-treated (30 mg/kg, i.v.) and NMA+ARG (arginine) (30 mg/kg and 60 mg/kg) was $46.2\pm3.8$ mm Hg and $33.6\pm3.2$ mm Hg, respectively (n=4-6). Points represent averages of the peak increases in mean systemic arterial pressure $\pm$S.E. observed after i.v. bolus of the indicated dose of phenylephrine or angiotensin II (n=4-6). FIGS. 1A and 1B depict the ability of phenylephrine (FIG. 1A)

and angiotensin II (FIG. 1B) to increase mean systemic arterial pressure, as a function of dose administered to control rats (non-pretreated) and rats that had been pretreated with endotoxin (LPS-pretreated) 6 hours prior to cardiovascular assessment. FIGS. 1A and 1B demonstrate that endotoxin pretreatment elicits a marked reduction in the maximal increases in arterial pressure due to the $\alpha_1$ adrenergic agonist phenylephrine (60%) and the pressor agent angiotensin II (85%). Thus, the animal model resembles the clinical condition of sepsis in this regard. FIGS. 1A and 1B further demonstrate that immediately after administration of a nitric oxide synthesis blocker, $N^G$-methyl-L-arginine (NMA), responses to both pressor drugs are restored to control levels. Subsequent administration of an excess of L-arginine, which overcomes NMA's inhibition of nitric oxide synthesis, restores the earlier observed diminished sensitivity to phenylephrine (see FIG. 1A). These results indicate that endotoxin-induced nitric oxide synthesis mediates the diminished pressor sensitivity in this animal model of sepsis.

EXAMPLE 2

In vitro Testing

Figure 2B:
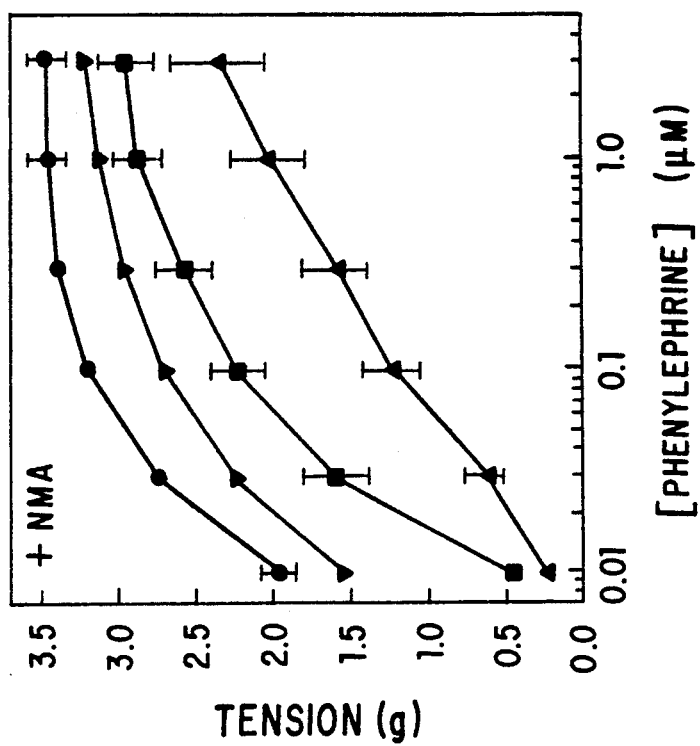
FIGS. 2A and 2B depict the effect of endotoxin (LPS; lipopolysaccharide) treatment of the rat on constriction of isolated aortic rings by phenylephrine in the absence (FIG. 2A) and presence (FIG. 2B) of 300 $\mu$M $N^G$-methyl-L-arginine.
Figure 2A:
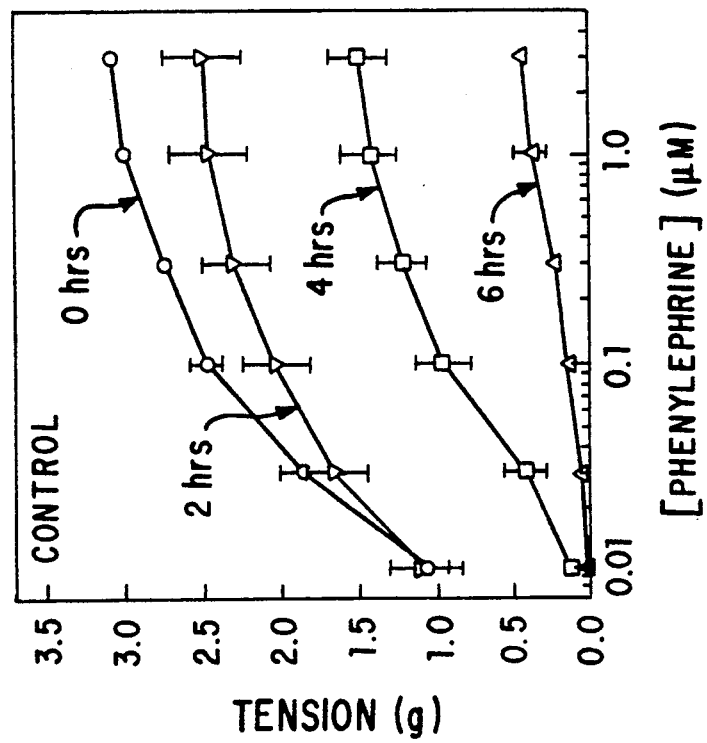

To confirm that the diminished responsiveness of endotoxic rats to pressor drugs has a vascular origin (rather than cardiac) we compared vasoconstrictor responses to ex vivo aortic rings isolated from control and endotoxic rats (FIGS. 2A and 2B). FIGS. 2A and 2B show the effect of LPS (lipopolysaccharide) treatment of the rat on constriction of isolated aortic rings by phenylephrine in the absence (FIG. 2A) and presence (FIG. 2B) of 300 $\mu$M $N^G$-methyl-L-arginine. Rats were either untreated or pretreated with LPS (15 mg/kg, i.p.) for the indicated duration (2, 4 or 6 hrs) prior to sacrifice and preparation of aortic rings for tension recording. Phenylephrine dose-response curves were constructed by cumulative administration. When rings were NMA treated, NMA was added 5 min prior to the first dose of phenylephrine and was continuously present throughout dose-response analysis. Points represent mean tension values $\pm$S.E. for tension generated by 5-8 aortic rings. As shown in FIG. 2A, the maximum constrictor response to phenylephrine decreases progressively as a function of the duration of endotoxin exposure in vivo. Note that by 6 hours after endotoxin treatment, the maximal phenylephrine response is less than 15% of control (0 hrs). FIG. 2B shows the effect of phenylephrine on these same vessels, however, in the presence of the nitric oxide synthesis inhibitor NMA. Notably, NMA significantly restores phenylephrine-induced vasoconstriction toward control levels. This find is consistent with the view that nitric oxide synthesis within the vascular wall is a major contributor to the endotoxin-induced reduction in vasoconstrictor response.

EXAMPLE 3

Serum Nitrate

Figure 3:
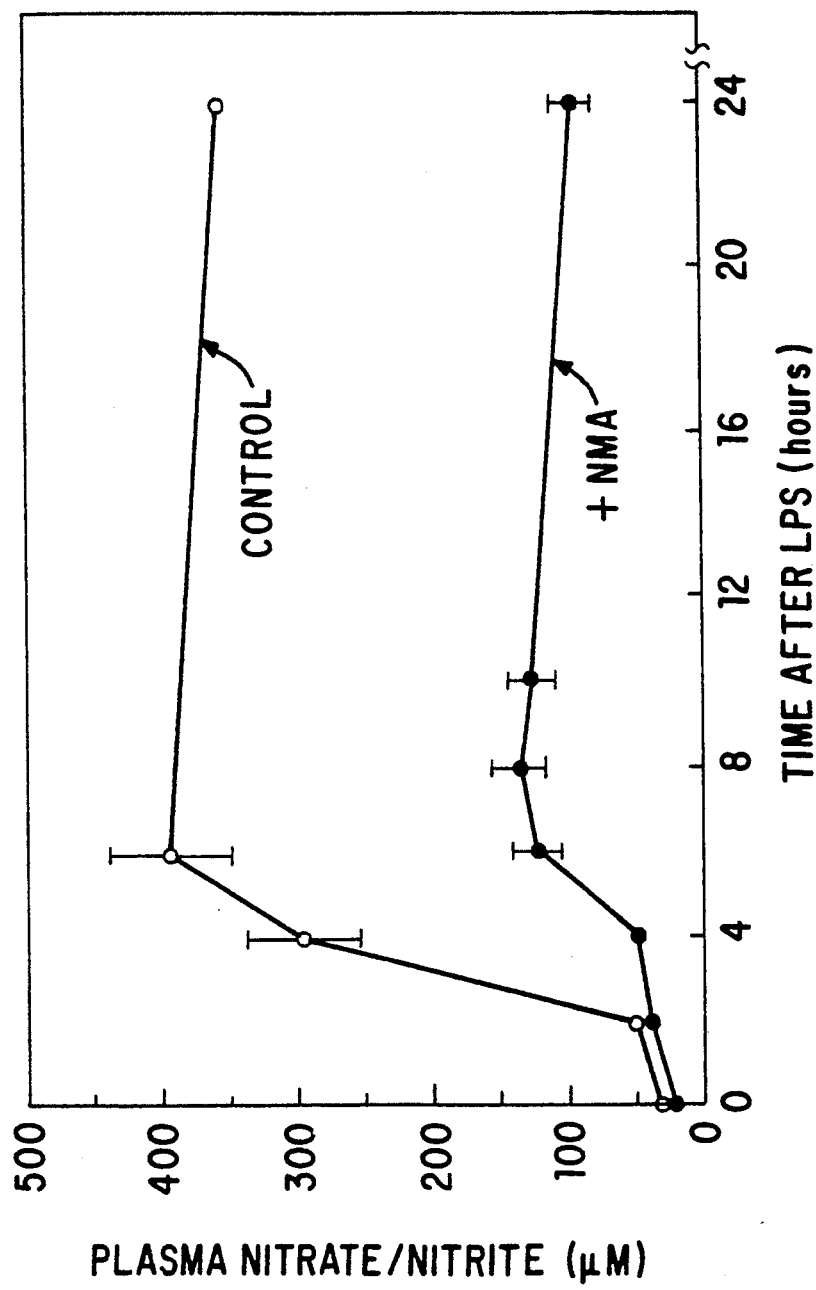
FIG. 3 depicts the time-course of LPS-induced elevation of serum levels of NO metabolites nitrate and nitrite, with or without $N^G$-methyl-L-arginine (NMA).

It is noteworthy that endotoxin elicits a greater than 15-fold increase in serum nitrate, an accumulating stable oxidation product of nitric oxide (FIG. 3). FIG. 3 shows the time-course of LPS-induced elevation of serum nitrate/nitrite with or without $N^G$-methyl-L-arginine (NMA). Points depict the mean levels $\pm$S.E. of nitrate/nitrite in rat serum as a function of time after administration of saline or LPS (15 mg/kg, i.p.) to control rats and animals continuously infused with NMA (n=4-6). NMA infusion was via osmotic minipumps which were implanted subcutaneously 3 hrs prior to LPS challenge and released NMA at a rate of 18 mg/kg/hr. The maximal increase in serum nitrate peaks after six hours, a time which coincides with the near-complete inhibition of phenylephrine-induced vasoconstriction. Furthermore, NMA infusion markedly dampens the increase in serum nitrate elicited by endotoxin in addition to restoring the constrictor response to phenylephrine.

EXAMPLE 4

Comparative Effectiveness of Arginine Antagonists for Restoration of $\alpha_1$ Receptor Response Endotoxic rings isolated from rats subjected to a dose of endotoxin were studied in terms of their contractile response to phenylephrine alone and in the presence of various arginine antagonists. L-arginine substituted on the guanidino group with $N^G$-methyl, nitro or amino was studied. All were found to restore the constrictor response to phenylephrine in aortic rings from endotoxic rats.

Figure 4:
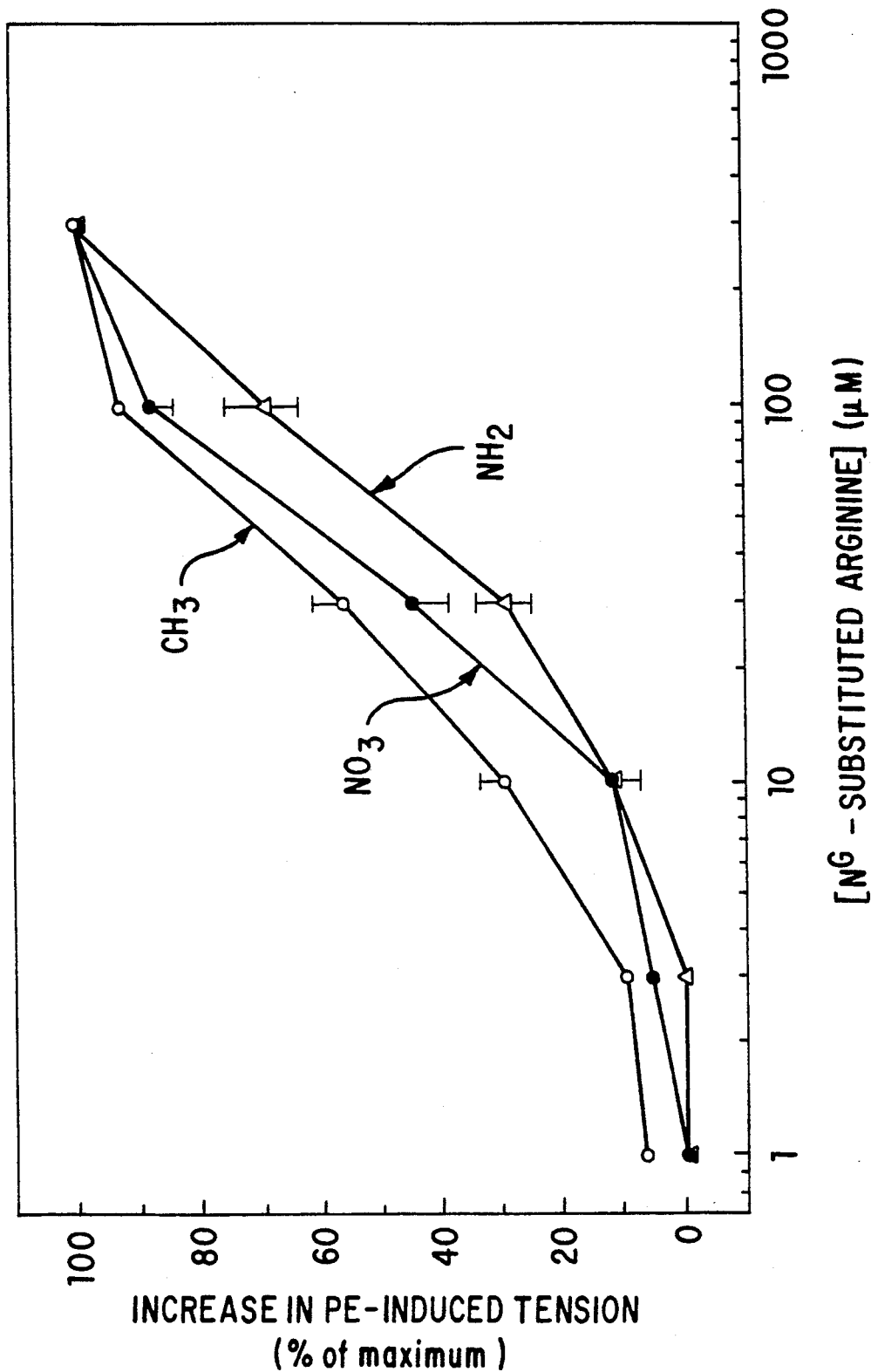
FIG. 4 shows a comparison of the potencies of $N^G$-methyl- and $N^G$-nitro- and $N^G$-amino-L-arginine for restoring phenylephrine (PE)-induced constriction in endotoxic aortic rings.

As FIG. 4 indicates, $N^G$-methyl arginine was more effective than $N^G$-nitro arginine, which in turn was more effective than $N^G$-amino arginine. All were nevertheless effective and in fact at the highest doses restored approximately the same sensitivity to phenylephrine. This observation further strengthens the role of nitric oxide induced by endotoxin or other cytokines as that substance which is responsible for the loss of sensitivity to pressor drugs such as the $\alpha_1$ adrenergic drugs.

EXAMPLE 5

METHODS

Blood pressure recording in the pithed rat

Sprague-Dawley rats (250-300 g) were anesthetized with ethyl ether and pithed as previously described by Shiply and Tilden (Shipley, R. E. and Tilden, J. H. (1947) A pithed rat preparation suitable for assay of pressor substances, *Proc Soc Exp Med*, 65:453-455). A tracheotomy was performed, and rats were artificially respired with room air. The left common carotid artery was cannulated for blood pressure measurement via a Statham pressure transducer (Hato Rey, Puerto Rico) and displayed on a physiograph (Grass Instruments, Quincy, Mass.). Heart rate was measured from the lead III electrocardiogram. Animals that were treated with endotoxin received a 15 mg/kg intraperitoneal dose, 6 hours prior to study. The left jugular vein was cannulated for bolus administration of pressor agents.

Assay of serum nitrate and nitrite

The combined concentration of nitrate and nitrite in rat serum was measured using an automated method. Briefly, diluted serum samples (5-10 $\mu$l) were injected via an automatic sample injector into a stream of 5% ammonium chloride buffer (brought to pH 8.0 with sodium borate) and pumped at a rate of 1 ml/min. The sample passed through a copper-coated cadmium column which catalytically reduced nitrate to nitrite. Subsequently, nitrite was derivatized on-line with Griess reagent (0.05% napthalenediamine and 0.5% sulfanilamide in 5% orthophosphoric acid; flow rate of 1 ml/min) to form an azo dye product which was assayed at $OD_{543}$ using a flow-through spectrophotometer (Pharmacia; Upsalia, Sweden).

Changes may be made in the pressor drugs, inhibitors of NO synthesis from arginine or method steps of the present claimed invention without departing from the scope and spirit of the following claims.

What is claimed is:

1. A method for treatment of a patient having systemic hypotension induced by administration of gamma-interferon, tumor necrosis factor, interleukin-1 or interleukin-2, said method involving intravascularly administering to the patient an $\alpha_1$ adrenergic agonist and an amount of an inhibitor of nitric oxide synthesis from arginine to the patient, wherein the amount of nitric oxide synthesis inhibitor restores vascular sensitivity to effects of the $\alpha_1$ adrenergic agent.

2. The method of claim 1 wherein the nitric oxide synthesis inhibitor is an arginine derivative.

3. The method of claim 2 wherein the arginine derivative is an $N^G$-substituted arginine or an $N^G,N^G$-disubstituted arginine and the $N^G$-substituted arginine or $N^G,N^G$-disubstituted arginine has at least one nitro, amino, lower alkyl, hydroxyalkyl or alkenyl substituent replacing a guanidino amino hydrogen.

4. A method for treatment of a patient for systemic hypotension induced by exposure to endotoxin or other bacterial toxins, said method involving intravascularly administering to the patient an $\alpha_1$ adrenergic agonist and an amount of an inhibitor of a nitric oxide synthesis from arginine, wherein the amount of nitric oxide synthesis inhibitor restores vascular sensitivity to the $\alpha_1$ adrenergic agent.

5. The method of claim 4 wherein the inhibitor is an arginine derivative.

6. The method of claim 4 wherein the nitric oxide synthesis inhibitor is an $N^G$-substituted arginine or $N^G,N^G$-disubstituted arginine and the $N^G$-substituted arginine or $N^G,N^G$-disubstituted arginine has at least one nitro, amino, lower alkyl, hydroxyalkyl or alkenyl substituent replacing a guanidino amino hydrogen.

7. The method of claim 3 or 6 wherein the $N^G$-substituted arginine is $N^G$-aminoarginine, $N^G$-nitroarginine, $N^G$-methylarginine, $N^G$-ethylarginine, $N^G$-propylarginine or $N^G$-butylarginine.

8. The method of claim 3 or 6 wherein the $N^G$-substituted arginine or $N^G,N^G$-disubstituted arginine is an $N^G$-alkylarginine or $N^G,N^G$-dialkylarginine.

9. The method of claim 2, 3 or 6 wherein the $N^G$-substituted arginine or $N^G,N^G$-disubstituted arginine are L-arginine derivatives.

10. A method for treatment of a patient for systemic hypotension caused by induced production, by cytokine administration or exposure to endotoxin, of nitric oxide, said method involving administering to a patient an $\alpha_1$ adrenergic agonist and an arginine derivative in an amount inhibiting production of nitric oxide from arginine, this inhibition being effective to restore vascular sensitivity to effects of the $\alpha_1$ adrenergic agonist.

11. A method for treatment of a patient for systemic hypotension caused by nitric oxide production induced by gamma-interferon, tumor necrosis factor, interleukin-1, or interleukin-2, said method involving intravascularly administering to the patient an $\alpha_1$ adrenergic agonist and an amount of an arginine derivative inhibiting production of nitric oxide from arginine.

12. A method for treatment of a patient for systemic hypotension induced by therapy with gamma-interferon, tumor necrosis factor, interleukin-1 or interleukin-2, said method involving intravascularly administering to the patient an $\alpha_1$ adrenergic agonist and an amount of $N^G$-alkylarginine, $N^G,N^G$-dialkylarginine, $N^G$-aminoarginine or $N^G$-nitroarginine effective to restore vascular sensitivity to the $\alpha_1$ adrenergic agonist.

13. The method of claim 12 wherein the $N^G$-alkylarginine and $N^G,N^G$-dialkylarginine have at least one alkyl substituent selected from the group consisting of methyl, ethyl, propyl and butyl.

14. The method of claim 12 wherein the alkyl of the $N^G$-alkylarginine and $N^G,N^G$-dialkylarginine are derivatized and selected from the group consisting of hydroxyalkyl, carboxyalkyl and aminoalkyl.

15. A method for treatment of a patient for systemic hypotension induced by exposure to endotoxin or other bacterial toxins, the method involving administering to the patient an $\alpha_1$ adrenergic agonist and an amount of $N^G$-alkylarginine, $N^G,N^G$-dialkylarginine, $N^G$-aminoarginine or $N^G$-nitroarginine effective to inhibit nitric oxide production and restore vascular sensitivity to the $\alpha_1$ adrenergic agonist.

16. A method for treatment of a patient for systemic hypotension caused by induced production, by an administered cytokine or endotoxin exposure, of nitric oxide from arginine, said method involving intravascularly administering to the patient an $\alpha_1$ adrenergic agonist and an amount of an inhibitor of production of nitric oxide from arginine.

17. A method for treatment of a patient for systemic hypotension caused by nitric oxide production induced by exposure to endotoxin or other bacterial toxins, said method involving intravascularly administering to the patient an $\alpha_1$ adrenergic agonist and an amount of an arginine derivative inhibiting production of nitric oxide from arginine being effective to restore vascular sensitivity to the $\alpha_1$ adrenergic agonist.

18. A method for treatment of a patient with systemic hypotension caused by nitric oxide production induced by endotoxin or other bacterial toxins, said method involving intravascularly administering to the animal an $\alpha_1$ adrenergic agonist and an amount of an arginine derivative effective to inhibit nitric oxide production and restore vascular sensitivity to the $\alpha_1$ adrenergic agonist, said arginine derivative being arginine with at least one $N^G$ substituent selected from the group consisting of amino, nitro, alkyl, hydroxyalkyl and alkenyl.

19. A method for treatment of a patient for systemic hypotension induced by treatment with gamma-interferon, tumor necrosis factor, interleukin-1 or interleukin-2 said method involving intravascularly administering to the patient an $\alpha_1$ adrenergic agonist and an amount of $N^G$-methylarginine effective to inhibit nitric oxide production and restore vascular sensitivity to the $\alpha_1$ adrenergic agonist.

20. A method for treatment of a patient for systemic hypotension caused by production of a nitrogen oxide induced by exposure to endotoxin or other bacterial toxins, said method involving intravascularly administering to the patient an $\alpha_1$ adrenergic agonist and an amount of $N^G$-methylarginine effective to inhibit nitric oxide production and restore vascular sensitivity to the $\alpha_1$ adrenergic agonist.

21. The method of claim 19 or 20 wherein the effective amount is between about 0.1 mg/kg and about 100 mg/kg.

22. The method of claim 19 or 20 wherein the $N^G$-methylarginine is $N^G$-methyl L-arginine.

23. A method for treatment of a patient for systemic hypotension induced by chemotherapeutic treatment with tumor necrosis factor or interleukin-2, said method involving administering to the patient an $\alpha_1$ adrenergic agonist and an amount of $N^G$-substituted arginine or an $N^G,N^G$-disubstituted arginine effective to inhibit nitric oxide production and restore vascular sensitivity to the $\alpha_1$ adrenergic agonist, wherein the $N^G$-substituted or $N^G,N^G$-disubstituted arginine has a nitro, amino, alkyl, hydroxyalkyl or alkenyl substituent replacing at least one hydrogen of a guanidino amino group.

24. The method of claim 23 wherein the administering is parenteral.

25. The method of claim 24 wherein the parenteral administering is intravascular.

26. The method of claim 1, 4, 10, 11, 12, 15, 16, 17, 18, 19, 20 or 23 wherein the $\alpha_1$ adrenergic agonist is selected from the group consisting of epinephrine, norepinephrine, dopamine, metaraminol, methoxamine, ephedrine and mephentermine.

27. The method of claim 1, 4, 10, 11, 12, 15, 16, 17, 18, 19, 20 or 23 wherein the $\alpha_1$ adrenergic agonist is selected from the group consisting of phenylephrine and angiotensin II.

* * * * *